United States Patent
Somoza et al.

(10) Patent No.: US 12,427,120 B2
(45) Date of Patent: Sep. 30, 2025

(54) COMPOSITIONS COMPRISING GUAIFENESIN AND FLAVOUR COMPOUNDS CONTAINING AN ISOVANILLYL GROUP

(71) Applicant: SYMRISE AG, Holzminden (DE)

(72) Inventors: Veronika Somoza, Weidling (AT); Leopoldo Beltran, Vienna (AT); Joachim Hans, Holzminden (DE); Jakob Ley, Holzminden (DE)

(73) Assignee: SYMRISE AG, Holzminden (DE)

( * ) Notice: Subject to any disclaimer, the term of this patent is extended or adjusted under 35 U.S.C. 154(b) by 781 days.

(21) Appl. No.: 17/284,323

(22) PCT Filed: Oct. 9, 2018

(86) PCT No.: PCT/EP2018/077513
§ 371 (c)(1),
(2) Date: Apr. 9, 2021

(87) PCT Pub. No.: WO2020/074073
PCT Pub. Date: Apr. 16, 2020

(65) Prior Publication Data
US 2021/0386686 A1    Dec. 16, 2021

(51) Int. Cl.
| | | |
|---|---|---|
| *A61K 31/09* | (2006.01) | |
| *A61K 9/00* | (2006.01) | |
| *A61K 45/06* | (2006.01) | |
| *A61K 47/26* | (2006.01) | |

(52) U.S. Cl.
CPC ............ *A61K 31/09* (2013.01); *A61K 9/0056* (2013.01); *A61K 9/0095* (2013.01); *A61K 45/06* (2013.01); *A61K 47/26* (2013.01)

(58) Field of Classification Search
CPC .............................. A61K 9/0095; A61K 47/26
See application file for complete search history.

(56) References Cited

U.S. PATENT DOCUMENTS

| | | | |
|---|---|---|---|
| 5,002,791 A | 3/1991 | Knebl | |
| 5,458,894 A | 10/1995 | Knebl et al. | |
| 6,391,886 B1* | 5/2002 | Lee | A61K 9/0034 514/289 |
| 6,432,441 B1 | 8/2002 | Bealin-Kelly et al. | |
| 2008/0014267 A1 | 1/2008 | Giordano et al. | |
| 2010/0292175 A1* | 11/2010 | Wessjohann | A23L 27/88 514/23 |
| 2017/0196898 A1* | 7/2017 | Rosa | A61K 31/137 |

FOREIGN PATENT DOCUMENTS

| | | | | |
|---|---|---|---|---|
| EP | 1258200 A2 | 11/2002 | | |
| EP | 1452177 A1 | 9/2004 | | |
| EP | 2220945 A1 | 8/2010 | | |
| EP | 2845606 A1 * | 3/2015 | ............. | A23L 33/10 |
| JP | 2003-300874 A | 10/2003 | | |
| WO | WO-2017/088936 A1 | 6/2017 | | |
| WO | WO-2017/186299 A1 | 11/2017 | | |
| WO | WO-2020035177 A1 * | 2/2020 | ............. | A23G 3/368 |

OTHER PUBLICATIONS

Ley et al. Evaluation of Bitter Masking Flavanones from Herba Santa, Journal of Agricultural and Food Chemistry, Jul. 2005, pp. 6061-6066. (Year: 2005).*
Brockhoff et al., "Receptor Agonism and Antagonism of Dietary Bitter Compounds," The Journal of Neuroscience, 31(41):14775-14782 (2011).
Gaudette et al., "The Contribution of Bitter Blockers and Sensory Interactions to Tlavour Perception," Chem. Percept. 9:1-7 (2016).
International Search Report from International Application No. PCT/EP2018/077513 dated Jun. 12, 2019.
Laboisse et al., "Characterization of a Newly Established Human Gastric Cancer Cell Line HGT-1 Bearing Histamine $H_2$-Receptors," Cancer Research 42:1541-1548 (1982).
Ley et al., "Evaluation of Bitter Masking Flavanones from Herba Santa (*Eriodictyon californicum* (H.& A.) Torr., Hydrophyllaceae)," J. Agric. Food Chem. 53:6061-6066 (2005).
Liszt et al., "Characterization of Bitter Compounds via Modulation of Proton Secretion in Human Gastric Parietal Cells in Culture," J. Agric. Food Chem., 66(10):2295-2300 (2018).
Office Action from European Application No. 18 785 922.8 dated Jun. 27, 2023.

* cited by examiner

*Primary Examiner* — San Ming R Hui
*Assistant Examiner* — Mikhail O'Donnel Robinson
(74) *Attorney, Agent, or Firm* — MARSHALL, GERSTEIN & BORUN LLP

(57) ABSTRACT

The present invention refers to a composition comprising guaifenesin and one or more flavour compound(s) containing an isovanillyl group. In particular, the present invention refers to a composition comprising guaifenesin and one or more flavour compound(s) containing an isovanillyl group, said composition being for medical use, in particular for use in the prevention and treatment of respiratory diseases. Moreover, the present invention relates to the use of guaifenesin and one or more flavour compounds containing an isovanillyl group for the preparation of a pharmaceutical composition. Finally, the present invention relates to the use of one or more flavour compound(s) containing an isovanillyl group for masking or inhibiting the bitter taste of guaifenesin or of guaifenesin comprising compositions.

17 Claims, No Drawings

COMPOSITIONS COMPRISING GUAIFENESIN AND FLAVOUR COMPOUNDS CONTAINING AN ISOVANILLYL GROUP

CROSS-REFERENCE TO RELATED APPLICATIONS

This is a U.S. National Phase of International Application No. PCT/EP2018/077513, filed Oct. 9, 2018, the contents of which are incorporated herein by reference.

FIELD OF THE INVENTION

The present invention refers to a composition comprising guaifenesin and one or more flavour compound(s) containing an isovanillyl group, respectively preferably isovanilloid compounds. In particular, the present invention refers to a composition comprising guaifenesin and one or more flavour compound(s) containing an isovanillyl group, said composition being for medical use, in particular for use in the prevention and treatment of respiratory diseases, more particularly for treating a common cold, cough or catarrh. Moreover, the present invention relates to the use of guaifenesin and one or more flavour compound(s) containing an isovanillyl group for the preparation of a pharmaceutical composition. Finally, the present invention relates to the use of one or more flavour compound(s) containing an isovanillyl group for masking or inhibiting the bitter taste of guaifenesin or of guaifenesin comprising compositions.

STATE OF THE ART

Guaifenesin is a pharmaceutically effective compound which belongs to the class of mucokinetics. Mucokinetics are a class of drugs which aid in the clearance of mucus from the respiratory airways, lungs, bronchi and tracheae. Such drugs can be further categorized by their mechanism of action, namely as mucolytic agents, expectorants, surfactants, wetting agents (hypoviscosity agents) and adhesives. In general, the clearance ability of mucokinetics is hampered by bonding to surfaces (stickiness) and by the viscosity of mucous secretions in the lungs. In turn, the viscosity is dependent upon the concentration of mucoprotein in the secretions.

Expectorants and mucolytic agents are different types of medication, yet both are intended to promote drainage of mucus from the lungs. An expectorant increases bronchial secretion, and mucolytics help loosen viscous bronchial secretions. Expectorants reduce the thickness or viscosity of bronchial secretions, thus increasing mucus flow, so that it can be removed more easily through coughing.

Guaifenesin or compositions comprising guaifenesin or one or more of its isomers in pharmacologically effective amounts are administered orally and offered in liquid or solid form, as for example syrups, sprays, tablets, pills, capsules, etc. Regardless of the galenic presentation, the products suffer from the same disadvantage, that is a bitter taste. Due to the bitter taste oral administration is unpleasant, and reduces patient compliance, especially when administered to children.

Typically, cough medicaments contain propylene glycol (1,2-propanediol) as a solvent. However, propylene glycol often enhances the bitterness of the active ingredients, so that products found in the market typically need to contain high amounts of sweeteners and/or aroma compounds to overcome or cover the bitter taste.

If pharmaceutical compositions have a bitter taste they may be mixed with a sweetening agent to mask the bitter taste. However, since some of the sweetening agents also have a bitter taste of their own, the use of sweetening agents for masking or inhibiting bitter taste is limited.

Document EP 1 452 177 A1 refers to a bitterness masking agent for pharmaceutical formulations. It was found that sodium laurylsulfate can mask the bitter taste of some bitter tasting pharmaceutically active compounds, in particular epinastine or quinine comprising formulations.

Homoeriodictyol (HED) was described as a masking agent for guaifenesin in Ley et al., J. Agric. Food Chem. 2005 (53), 6061 to 6066, FIG. 5, Example 2. In a relatively high concentration of 200 ppm (200 mg/l HED), i.e. 0.2 mg/ml HED against 13 mg/ml guaifenesin, a reduction in guaifenesin bitterness of about 40% was described.

Flavanones, as for example homoeriodictyol, eriodictyol or naringenin are described as bitter maskers in EP 1 258 200 A1 as exemplified for caffeine or in WO 2017/088936 A1 for omeprazole or pantoprazol. However, due to the very complex mechanisms behind human bitter taste reception and perception (Brockhoff, A.; Behrens, M.; Roudnitzky, N.; Appendino, G.; Avonto, C.; Meyerhof, W., Receptor agonism and antagonism of dietary bitter compounds, J. Neurosci., 2011, 31, 14775 to 14782), actually a potential bitter masking effect against other pharmaceutical active ingredients is not predictable due to missing or insufficient data on the agonistic/antagonistic bitter receptor activities of guaifenesin.

It is relatively common to use high impact sweeteners such as aspartame or thaumatin in order to camouflage the bitter taste of drugs. Nevertheless, the bitter taste in most cases is not really suppressed, but only overlayed with a strong sweet taste. Therefore, many patients are still complaining about bitter taste of such drugs, especially in the aftertaste.

Flavour compounds containing an isovanillyl group are known and often used as sweet taste eliciting or sweet taste modulating compounds, e.g. neohesperidindihydrochalcone, hesperetindihydrochalcone, hesperetin, and phyllodulcin. In relatively high concentrations they exhibit a sweet taste or can modulate the sweet taste. At a low level, typically they do not generate a sufficient sweet taste, but they were never reported to reduce the bitter taste of compounds such as guaifenesin in such low concentrations. There are also compounds which do not have any specific taste such as hesperidin, hesperetindihydrochalcone-4'-O-glucoside, or do not taste sweet, but bitter in higher concentrations, e.g. neohesperidin or hesperetin-7-glucoside or phyllodulcin-8-O-glucoside. Therefore, it is not obvious to use these compounds to mask the bitter taste of guaifenesin.

The object of the present invention, therefore, has been to provide a composition comprising guaifenesin for the prevention and treatment of respiratory diseases with improved taste, in particular with reduced or eliminated bitter taste. Another object of the present invention has been to find other compounds which can mask or inhibit the bitter taste of guaifenesin or of guaifenesin comprising compositions.

SUMMARY OF THE INVENTION

Hence, in a first aspect, the present invention relates to a composition, comprising
(a) guaifenesin or one or more of its derivatives or isomers or mixtures thereof, and (b) one or more flavour compound(s) containing an iso-vanillyl group or one or more of its/their derivatives or isomers or mixtures thereof; and (c) optionally at least one pharmaceutically acceptable adjuvant or additive.

In another aspect, the present invention relates to the use of the aforementioned composition for the preparation of pharmaceutical compositions and its use for the prevention and treatment of respiratory diseases.

In still another aspect, the present invention relates to providing one or more flavour compound(s) containing an isovanillyl group or one or more of its/their derivatives or isomers or mixtures thereof for masking or inhibiting the bitter taste of guaifenesin or of guaifenesin comprising compositions.

Preferred variants of the aforementioned composition are apparent from dependent claims and the detailed description of the invention.

DETAILED DESCRIPTION OF THE INVENTION

The first aspect of the present invention relates to a composition, comprising (a) guaifenesin or one or more of its derivatives or isomers or mixtures thereof, and (b) one or more flavour compound(s) containing an iso-vanillyl group or one or more of its/their derivatives or isomers or mixtures thereof; and (c) optionally at least one pharmaceutically acceptable adjuvant or additive.

Guaifenesin, also known as glyceryl guaiacolate, whose chemical name is 3-(2-methoxyphenoxy-)1,2-propanediol is an expectorant drug. The compound is represented by formula (1):

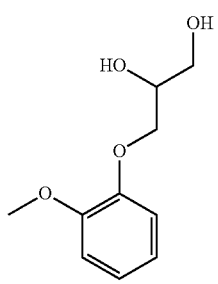

(1)

Guaifenesin exists in two stereo isomers, namely the R-enantiomer (formula (1R)) and the S-enantiomer (formula (1S)).

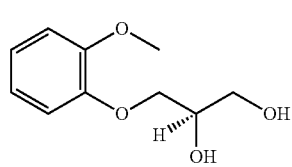

(1R)

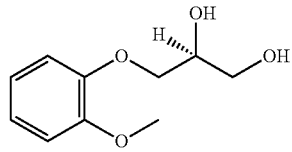

(1S)

Throughout the present invention, the term "guaifenesin" includes either the R-enantiomer, the S-enantiomer, mixtures of the R- and S-enantiomers, or the racemate. In a preferred embodiment of the present invention, guaifenesin may be used as the racemate.

In particular, guaifenesin may be used as a mixture of enantiomers in the range of molar amounts of from 0.1 2S:100 2R to 0.1 2R:100 2S, as pure enantiomers, preferred as a racemic mixture (50:50) or almost racemic mixtures of from 35 2S:65 2R to 65 2R:35 2S, preferably from 45 2S:55 2R to 55 2R:45 2S.

Moreover, the present invention encompasses also derivatives of guaifenesin such as methocarbamol, represented by formula (2):

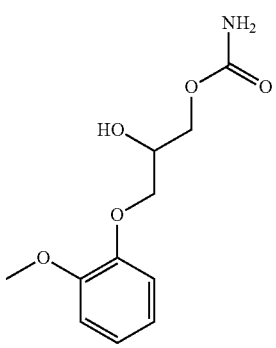

(2)

Furthermore, guaifenesin may be used in the form of its pharmaceutical acceptable salts, esters or mixtures thereof. In particular preferred are the mono- or divalent salts and the ammonium salt. Among the salts, sodium, calcium, magnesium, potassium or ammonium are most preferred.

Guaifenesin is thought to act by thinning the mucus, loosening phlegm and bronchial secretion, and also by lubricating the irritated respiratory tract. By thinning the mucus, guaifenesin reduces the viscosity of the mucus secretion, and as a result increases the efficiency of the cough reflex and of ciliary action in removing accumulated secretions from trachea and bronchi. The effect felt by an individual is that a non-productive cough becomes more productive and less frequent. Unfortunately, guaifenesin has an unpleasantly bitter taste.

Surprisingly, it has been observed that patients, to whom the composition according to the present invention was administered, find that the composition has a much better taste, in particular a significantly reduced bitter taste, compared to a similar product comprising the same amount of guaifenesin, but comprising no such a flavour compound/flavour compounds containing an isovanillyl group. It was found that the bitter taste of guaifenesin may be masked or even inhibited by at least one flavour compound containing an isovanillyl group used according to the present invention.

In accordance with the present invention, in a formulation containing guaifenesin, the use of one or more flavour compound(s) containing an isovanillyl group will serve to abate or eliminate the customary bitter taste attributable to the bitter-tasting agent, i.e. guaifenesin. The resulting formulation is therefore less bitter-tasting than it would otherwise expected from the formulation containing guaifenesin, i.e. resulting in a more pleasant tasting formulation.

In the context of the present invention, the term "masking" means a reduction, i.e. decrease, of the bitter taste. The term "inhibiting" means a complete suppression of the bitter taste.

In particular, when guaifenesin contained in a composition, preferably in a pharmacologically effective amount, is used in combination with one or more flavour compound(s) containing an isovanillyl group, the bitterness is reduced by at least 15%, preferably 25%, in particular about 35% or more. This is a significant improvement in particular in direct comparison to a comparable amount of the known state of the art masker homoeriodictyol. This effect is demonstrated in detail by the experimental data in Table 3.

An improvement in taste can be achieved by different strategies. Traditionally, an unpleasant bitter taste was diminished by the addition of pleasant flavouring substances, in order to merely cover the bitter taste. A second approach to suppress or inhibit bitter taste is to prevent contact of the bitter tasting compound with the bitter receptor in the mouth, specifically on the tongue of the person, to whom the composition containing the bitter tasting compound is administered. This may be achieved, for example, by encapsulation, molecular inclusion etc. of the bitter tasting compound. A third strategy of masking the bitter taste is the use of so-called taste receptor blockers (antagonists), which can reduce or inhibit the reaction of the taste receptor with the bitter tasting compound (agonist).

Up to now, the precise mechanism of action could not yet be determined according to which the masking action or inhibition of the bitter taste of guaifenesin works by use of a flavour compound containing an isovanillyl group.

The most prominent members of the flavour compounds containing an isovanillyl group are selected from the group consisting of flavanones comprising hesperetin (chemical name (2S)-/(2R)-5,7-dihydroxy-2-(3-hydroxy-4-methoxy-phenyl)-4-chromanone) or its O-glycosides, in particular hesperidin, neohesperidin or hesperetin-7-0-glucoside; and hesperetindihydrochalcone (chemical name 3-(3-hydroxy-4-methoxy-phenyl)-1-(2',4',6'-trihydroxyphenyl)propan-1-one) or its O-glycosides, in particular hesperidindihydrochalcone, neohesperidindihydrochalcone, or hesperetindihydrochalcone-4'-O-glucoside; and isocoumarines comprising phyllodulcin (chemical name (3S)-/(3R)-8-hydroxy-3-(3-hydroxy-4-methoxy-phenyl)isochroman-1-one) or its O-glycosides, in particular phyllodulcin-8-O-glucoside. Whereas the flavanones occur as such or as degradation products in citrus-derived preparations, the dihydrochalcones are prepared by hydrogenation from the respective flavanones and the isocoumarine phyllodulcin and derivatives thereof occur in certain *Hydrangea macrophylla* plant cultivars.

In this context, a first preferred variant of the first aspect of the present invention relates to a composition, wherein the one or more flavour compound(s) is/are selected from the group consisting of hesperetin, hesperidin, neohesperidin, hesperetin-7-O-glucoside, hesperetindihydrochalcone, hesperidindihydrochalcone, neohesperidindihydrochalcone, hesperetindihydrochalcone-4'-O-glucoside, phyllodulcin and phyllodulcin-8-O-glucoside. More preferred are in particular hesperetin, hesperetindihydrochalcone and phyllodulcin as one or more flavour compounds of the composition of the first aspect.

The O-glycosides of the above hesperetin or hesperetindihydrochalcone compounds are selected from the group consisting of the O-glucosides, O-(6O-alpha-L-rhamnosyl-beta-D-glucosides) (O-rutinosides), and O-(2O-alpha-L-rhamnosyl-beta-D-glucosides) (O-neohesperidosides). Preferred are the O-rutinosides of hesperetin or the O-neohesperidosides of hesperetindihydrochalcone.

The structures of the preferred flavour compounds are represented by the following formulae (3a) to (3j):

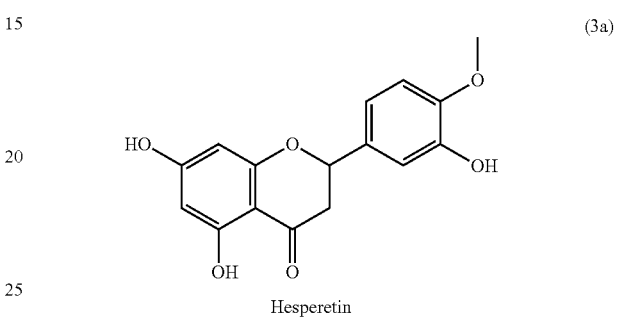

(3a)

Hesperetin

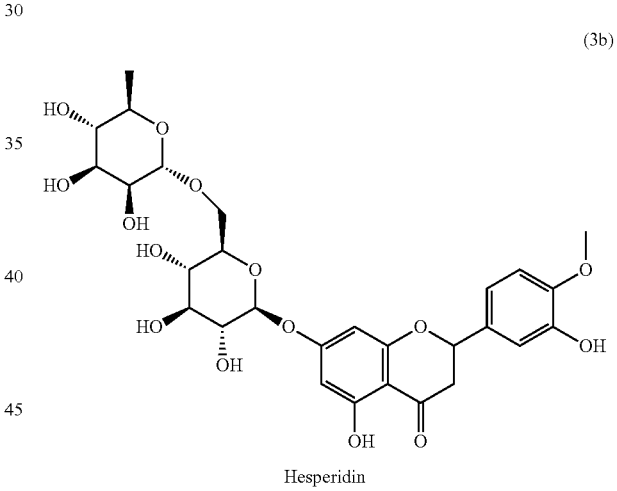

(3b)

Hesperidin

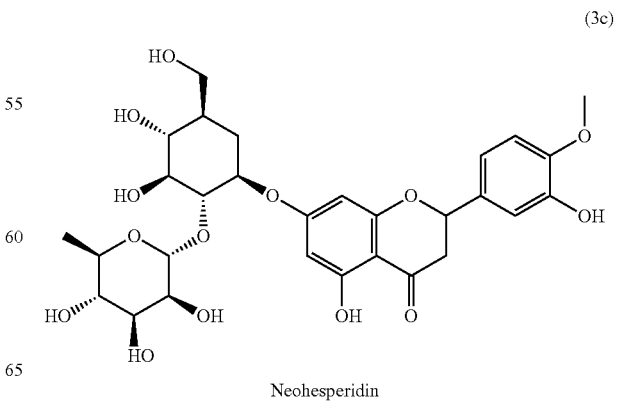

(3c)

Neohesperidin

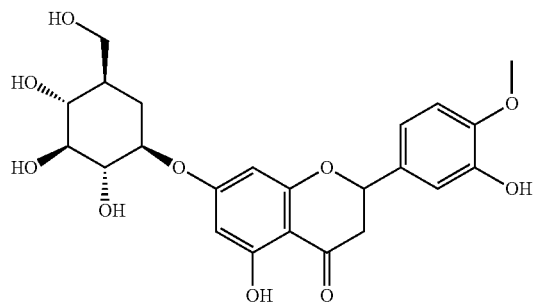
Hesperetin-7-O-glucoside

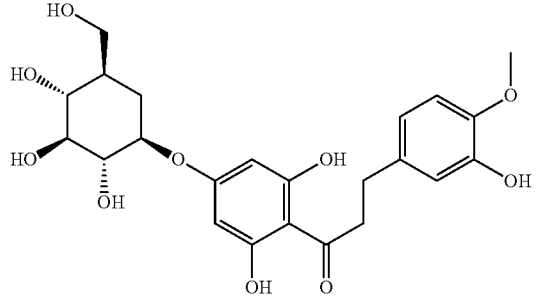
Hesperetindihydrochalcone-4'-O-glucoside

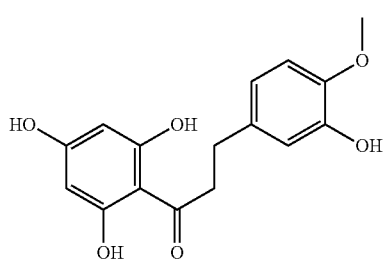
Hesperetindihydrochalcone

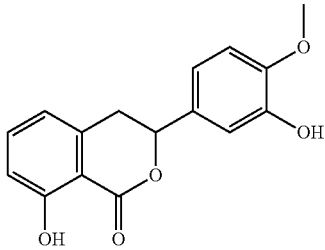
Phyllodulcin

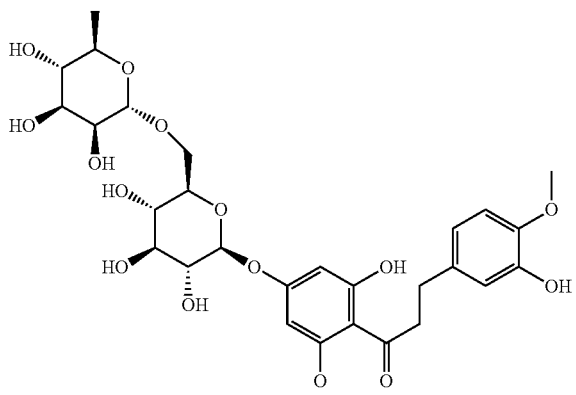
Hesperidindihydrochalcon

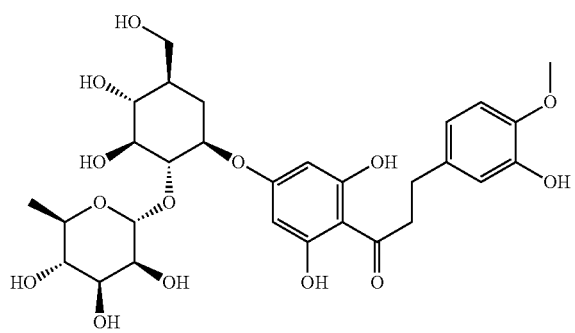
Neohesperidindihydrochalcone

<div style="page-break"></div>

Phyllodulcin-8-O-glucoside

Among the above-mentioned flavour compounds containing an isovanillyl group hesperetin, hesperetindihydrochalcone and phyllodulcin are preferred.

In the context of the present invention, the term "one or more flavour compound(s)" means either one single flavour compound containing an isovanillyl group or a combination of two, three, four or even five flavour compounds containing an isovanillyl group. In particular preferred are combinations of two or three flavour compounds containing an isovanillyl compound. Examples of such combinations include, but are not limited to the following combinations:

hesperetin and hesperidin and/or neohesperidin and/or hesperetin-7-O-glucoside and/or hesperetindihydrochalcone and/or hesperidindihydrochalcone and/or neohesperidindihydrochalcone and/or hesperetindihydrochalcone-4'-O-glucoside and/or phyllodulcin and/or phyllodulcin-8-O-glucoside; or hesperidin and neohesperidin and/or hesperetin-7-O-glucoside and/or hesperetindihydrochalcone and/or hesperidindihydrochalcone and/or neohesperidindihydrochalcone and/or hesperetindihydrochalcone-4'-O-glucoside and/or phyllodulcin and/or phyllodulcin-8-O-glucoside and/or hesperetin; or neohesperidin and hesperetin-7-O-glucoside and/or hesperetindihydrochalcone and/or hesperidindihydrochalcone and/or neohesperidindihydrochalcone and/or hesperetindihydrochalcone-4'-O-glucoside and/or phyllodulcin and/or phyllodulcin-8-O-glucoside and/or hesperetin and/or hesperidin; or hesperetin-7-O-glucoside and hesperetindihydrochalcone and/or hesperidindihydrochalcone and/or neohesperidindihydrochalcone and/or hesperetindihydrochalcone-4'-O-glucoside and/or phyllodulcin and/or phyllodulcin-8-O-glucoside and/or hesperetin and/or hesperidin and/or neohesperidin; or hesperetindihydrochalcone and hesperidindihydrochalcone and/or neohesperidindihydrochalcone and/or hesperetindihydrochalcone-4'-O-glucoside and/or phyllodulcin and/or phyllodulcin-8-O-glucoside and/or hesperetin and/or hesperidin and/or neohesperidin and/or hesperetin-7-O-glucoside; or neohesperidindihydrochalcone and/or hesperetindihydrochalcone-4'-O-glucoside and/or phyllodulcin and/or phyllodulcin-8-O-glucoside and/or hesperetin and/or hesperidin and/or neohesperidin and/or hesperetin-7-O-glucoside and/or hesperetindihydrochalcone and/or hesperidindihydrochalcone; or hesperetindihydrochalcone-4'-O-glucoside and phyllodulcin and/or phyllodulcin-8-O-glucoside and/or hesperetin and/or hesperidin and/or neohesperidin and/or hesperetin-7-O-glucoside and/or hesperetindihydrochalcone and/or hesperidindihydrochalcone and/or neohesperidindihydrochalcone; or phyllodulcin and phyllodulcin-8-O-glucoside and/or hesperetin and hesperidin and/or neohesperidin and/or hesperetin-7-O-glucoside and/or hesperetindihydrochalcone and/or hesperidindihydrochalcone and/or neohesperidindihydrochalcone and/or hesperetindihydrochalcone-4'-O-glucoside; or phyllodulcin-8-O-glucoside and hesperetin and hesperidin and/or neohesperidin and/or hesperetin-7-O-glucoside and/or hesperetindihydrochalcone and/or hesperidindihydrochalcone and/or neohesperidindihydrochalcone and/or hesperetindihydrochalcone-4'-O-glucoside and/or phyllodulcin.

The most preferred combinations are hesperetin and hesperetindihydrochalcone and phyllodulcin; or hesperetin and phyllodulcin; or hesperetindihydrochalcone and phyllodulcin.

The afore described flavanones or isocoumarines or their glycosides exists in each of two stereo isomers, namely the 2R- or 3R-enantiomer and the 2S- or 3S-enantiomer. Throughout the present invention, the compounds include either the 2R-enantiomer, the 3R-enantiomer, the 2S-enantiomer or the 3S-enantiomer, mixtures of the 2R-enantiomer, the 3R-enantiomer, the 2S-enantiomer or the 3S-enantiomer, or the racemates. In a preferred embodiment of the present invention, the compounds may be used as racemates in respect to the 2- or 3-position.

In particular, the afore described flavour compounds containing an isovanillyl group, i.e. flavanones or isocoumarines or their glycosides, may be used as mixture of enantiomers in the range of molar amounts of from 0.1 S:100 R to 0.1 R:100 S, as pure enantiomers, preferred as racemic mixture (50:50) or almost racemic mixtures of from 35 S:65 R to 65 R:35 S, preferably from 45 S:55 R to 55 R:45 S.

Moreover, the present invention encompasses also derivatives of the flavour compounds containing an isovanillyl group. Preferably, the compounds are used in the form of their pharmaceutical acceptable salts, esters or mixtures thereof. In particular preferred are the mono- or divalent salts and the ammonium salt. Among the salts, sodium, calcium, magnesium, potassium or ammonium are most preferred.

Further, in view of the above, a second variant of the present disclosure relates to a composition according to the first aspect, wherein the derivatives of guaifenesin or the one or more flavour compound(s) containing an isovanillyl group are selected from the group consisting of the salts, esters and mixtures of guaifenesin or of the flavour compound(s) containing an isovanillyl group. Herein, in particular preferred are mono- or divalent salts as well as ammonium salts. Even more preferred are salts selected from the group comprising sodium, calcium, magnesium, potassium and ammonium.

The amount of the one or more flavour compound(s) containing an isovanillyl group used, including the amount of all enantiomers and/or derivatives (e.g. salts, esters or mixtures thereof) of the flavour compounds containing an isovanillyl group used, depends on the amount of the bitter tasting ingredient guaifenesin contained in the composition. The amount of the one or more flavour compound(s) is any amount which is effective to mask or inhibit the bitter taste of guaifenesin. In the invention, the amount sufficient to mask or even inhibit the bitter taste could be determined.

In preferred formulations according to another variant of the first aspect, the composition of the present invention comprises guaifenesin in an amount of from 2000 to 20000 ppm. More preferred is an amount of from 5000 to 20000 ppm, and most preferred is an amount of from 5000 to 15000 ppm.

In a further preferred variant of the first aspect, the composition of the present invention comprises the one or more flavour compound(s) containing an isovanillyl group in a total amount of from 4 to 400 ppm. More preferred is a total amount of from 10 to 200 ppm, and most preferred is a total amount of from 10 to 50 ppm.

With regard to the bitter masking or inhibiting effect, the concentration of the one or more flavour compound(s) containing an isovanillyl group towards guaifenesin within the composition is decisive. Surprisingly, the bitter taste can be reduced or even inhibited most advantageously, if the one or more flavour compound(s) containing an isovanillyl group is/are used in an amount of 4 to 400 ppm, preferably in an amount of 10 to 50 ppm and guaifenesin is used in an amount of 2000 to 20000 ppm, preferably in an amount of 5000 to 15000 ppm.

Moreover, in another variant of the first aspect, the composition according to the present invention may comprise guaifenesin (compound (a)) and the one or more flavour compound(s) containing an isovanillyl group (compound (b)) in a ratio (w/w) from 5:1 to 5000:1. Preferably, the ratio (w/w) of guaifenesin (compound (a)) to the one or more flavour compound(s) containing an isovanillyl group (compound (b)) in the composition of the present invention is from 12.5:1 to 5000:1. More preferably the ratio (w/w) of guaifenesin (compound (a)) to the one or more flavour compound(s) containing an isovanillyl group (compound (b)) in the composition of the present invention is from 12.5:1 to 3750:1. In a more preferred embodiment, in the composition of the present invention the ratio (w/w) of guaifenesin (compound (a)) to the one or more flavour compound(s) containing an isovanillyl group (compound (b)) is from 10:1 to 2000:1, more preferably from 25:1 to 2000:1 and most preferably from 25:1 to 500:1. In still further preferred embodiments, the composition according to the present invention may comprise guaifenesin (compound (a)) and the one or more flavour compound(s) containing an isovanillyl group (compound (b)) in a ratio (w/w) from 40:1 to 2000:1, more preferably from 100:1 to 2000:1 and most preferably from 100:1 to 1500:1. The indication w/w stands for weight per weight of the composition.

In another variant of the first aspect, the present invention relates to a composition further comprising homoeriodictyol or eriodictyol or derivatives or isomers thereof or mixtures of both homoeriodictyol and eriodictyol.

Surprisingly, the bitter taste can still be further reduced or even inhibited, if the composition comprises homoeriodictyol (HED) whose chemical name is (2S)-/(2R)-5,7-Dihydroxy-2-(4-hydroxy-3-methoxyphenyl)-4-chromanone and/or eriodictyol whose chemical name is (2S)-/(2R)-5,7-Dihydroxy-2-(3,4-dihydroxyphenyl)-4-chromanone.
Homoeriodictyol and eriodictyol each exist in two stereo isomers, namely the 2R-enantiomer and the 2S-enantiomer. Throughout the present invention, the term "homoeriodictyol" or "eriodictyol" includes either the 2R-enantiomer, the 2S-enantiomer, mixtures of the 2R-enantiomer and the 2S-enantiomer, or the racemate.

Moreover, the present invention and in particular the present variant of the first aspect encompasses also derivatives of homoeriodictyol and/or eriodictyol. Preferably, homoeriodictyol and/or eriodictyol is/are used in the form of its/their pharmaceutical acceptable salts, esters or mixtures thereof. In particular preferred are the mono- or divalent salts and the ammonium salt. Among the salts, sodium, calcium, magnesium, potassium or ammonium are most preferred.

If the one or more flavour compound(s) is/are used in combination with homoeriodictyol and/or eriodictyol, the bitter masking effect can be increased significantly, as it is demonstrated by the following application examples. In a preferred embodiment of the present invention, there is even a synergistic effect, if the one or more flavour compound(s) containing an isovanillyl group and homoeriodictyol and/or eriodictyol are used in combination in the inventive composition.

In addition to the above ingredients, the inventive formulation may also comprise further pharmaceutically effective ingredients. In this context, a further variant of the first aspect relates to a composition, further comprising pharmaceutical effective compounds, preferably such compounds selected from the group comprising: analgesic agents, anti-inflammatory agents, antitussives, decongestants and antihistamines. Herein, it is preferred for each of the pharmaceutical compounds of the group consisting of analgesic agents, anti-inflammatory agents, antitussives, decongestants and antihistamines to be selected independently from one another.

Further, it is especially preferred for the effective pharmaceutical ingredients to be selected from the group, consisting of acetaminophen, phenylephrine, dextromethorphan, aspirin, ibuprofen, diphenhydramine, antihistamines, naproxen sodium and their mixtures.

Moreover, the composition can contain one or more additional pharmaceutically effective agents selected from the group including, but not limited to, an antitussive such as dextromethorphan hydrobromide, a decongestant such as phenylephrine hydrochloride, pseudoephedrine hydrochloride or ephedrine, an antihistamine such as chlorpheniramine maleate, brompheniramine maleate, phenindamine tartrate, pyrilamine maleate, doxylamine succinate, phenyltoloxamine citrate, diphenhydramine hydrochloride, promethazine, clemastine fumerate or fexofenadine or combinations thereof.

The composition according to the present invention usually contains at least two, often three, or even all of the aforementioned specified compounds. The amounts of the aforementioned pharmaceutically effective ingredients within the composition is about 0.1 to about 5% by weight, preferably about 0.5 to about 3% by weight and particularly about 1 to about 2% by weight.

The composition can have an immediate release portion or a sustained release portion, such that the promotion of mucus secretion is therapeutically achieved for a period of approximately 12 hours.

In addition to guaifenesin, the one or more flavour compound(s) containing an isovanillyl group and the above additional pharmaceutically effective ingredients, the formulation according to another variant of the first aspect of the present invention optionally may preferably comprise other pharmaceutically acceptable adjuvants and additives conventionally used for pharmaceutical preparations to be administered orally.

In particular, the present variant relates to a composition according to the first aspect of the invention, wherein the at least one adjuvant is selected from the group consisting of carriers, solvents, emulsifiers, dispersing agents, synthetic and natural biopolymers, stabilizers, colourings, pH-adjusting agents, flow agents, disintegrants, odour-correcting agents and taste-correcting agents.

The adjuvants include but are not limited to inter alia carriers (e.g. microcrystalline cellulose), solvents (e.g. liquid polyethylene glycols), emulsifiers (e.g. sodium dodecylsulfate), dispersing agents (e.g. polyvinyl pyrrolidone), synthetic and natural biopolymers (e.g. albumin) stabilizers (e.g. antioxidants such ascorbic acid), colourings (e.g. inorganic pigments) and odour-correcting agents as well as taste-correcting agents that do not affect the masking or inhibition of the bitter taste.

Optionally, the formulation according to the present invention may comprise additive sweetening agents to mask a quick-acting and a lasting bitter taste caused by guaifenesin. To mask the quick-acting bitter taste, cyclamate or its sodium salt, saccharin or its sodium salt, sucralose, acesulfam K, aspartame, thaumatin, advantam, neotam, glycyrrhicinic acid or its ammoniumsalt, or steviosides (e.g. stevioside, rebaudioside A, rebaudioside C, rebaudioside D, rebaudioside M, rubusoside) turned out to be effective.

Surprisingly, the bitter masking effect is even synergistic, if the one or more flavour compound(s) containing an isovanillyl group and the aforementioned sweeteners are used in combination in the inventive composition. In particular, a combination of the one or more flavour compound(s) containing an isovanillyl group and sweeteners such as cyclamate or its sodium salt, saccharin or its sodium salt, sucralose, acesulfam K, aspartame, glycyrrhicinic acid or its ammonium salt, stevioside, rebaudioside A, rebaudioside M or rubusoside turned out to be most effective in the masking or inhibiting the bitter taste of guaifenesin or a composition comprising guaifenesin.

Some of the aforementioned sweeteners, e.g. cyclamate or its sodium salt, saccharin or its sodium salt, acesulfam K, stevioside, rebaudioside A, exhibit a bitter taste, in particular a bitter aftertaste. Due to the known masking effect of homoeriodictyol against bitter taste of some sweeteners (Gaudette, N. J.; Delwiche, J. F.; Pickering, G. J., The contribution of bitter blockers and sensory interactions to flavour perception, Chemosensory Perception, 2015, 9 (1), 1 to 7), the combination of the one or more flavour compound(s) containing an isovanillyl group, homoeriodictyol, a sweetener and guaifenesin is in particular effective, as it is demonstrated by the following application examples, and preferred.

Another suitable group of sweet tasting compounds comprises sugars and sugar-derived polyols such as sucrose, glucose, fructose, allulose, trehalose, arabinose, D-sorbitol, palatinose, erythritol, xylitol, glycerin and D-mannitol.

The amount of these sweetening agents to mask the quick-acting bitterness depends of the agent used. In case of saccharin sodium, the amount is between 0.1% by weight and 2.0% by weight of a powder formulation. Preferably the amount is 0.8% by weight. In case of aspartame the amount is between 1% by weight and 30% by weight of a powder formulation. Preferably the amount is 5 to 15% by weight, most preferred it is 10% by weight.

For masking the lasting bitterness, glycyrrhizinates were found to be highly effective. Among them, glycyrrhizinic acid and/or monoammonium glycyrrhizinate are the preferred ones. The most preferred one is monoammonium glycyrrhizinate.

The amount of monoammonium glycyrrhizinate in a powder formulation is from 0.1% by weight to 3.0% by weight. More preferred are 0.1 to 1% by weight, and most preferred is 0.6% by weight.

Other kinds of adjuvants or additives are pH-adjusting agents to adjust the pH of the resulting composition to a value of preferably between 5 and 8, preferably 6 and 7. Among those agents are citric acid, succinic acid, tartaric acid, acetic acid, citrates, acetates, vitamin C, hydrochloric acid, carbonates, phosphates, disodium phosphate, monosodium phosphate, sodium, calcium, potassium and/or magnesium hydroxide. Preferred are buffer substances like disodium phosphate.

Further, other commonly used additives can optionally be added. Among these are binding agents such as for example hydroxypropylcellulose, methylcellulose, hydroxypropylmethylcellulose, hydroxyethylcellulose, starch, dextrin, gelatine and polyvinylpyrrolidone, preferably hydroxypropylcellulose, flow agents such as for example hydrated silicon dioxide or light anhydrous silicic acid or disintegrants such as for example starch, cellulose and derivatives, microcrystalline cellulose, alginates, bicarbonates or carbonates in combination with citric acid or tartaric acid.

According to another preferred embodiment of the present invention, the composition may contain at least one aroma compound, preferably at least one traditional flavour or a flavour modulating compound, which is different from the one or more aforementioned flavour compound(s) containing an isovanillyl group, in order to complete and refine the taste and/or odour of the composition.

Such compounds can be chosen from synthetic flavouring liquid and/or oils derived from plants leaves, flowers, fruits and so forth, and combinations thereof. Representative flavouring liquids include: artificial, natural or synthetic fruit flavours such as eucalyptus, mint (peppermint, spearmint), lemon, orange, banana, grape, lime, apricot and grapefruit oils and fruit essences including apple, strawberry, cherry, orange, pineapple and so forth; bean and nut derived flavours such as coffee, cocoa, cola, peanut, almond and so forth; and root derived flavours such as liquorice or ginger.

The flavouring agent is preferably selected from the group consisting of essential oils and extracts, tinctures and balsams, such as, for example, anisole, basil oil, bergamot oil, bitter almond oil, camphor oil, citronella oil, lemon oil; *Eucalyptus citriodora* oil, eucalyptus oil, fennel oil, grapefruit oil, chamomile oil, spearmint oil, caraway oil, lime oil, mandarin oil, nutmeg oil (in particular nutmeg blossom oil), myrrh oil, clove oil, clove blossom oil, orange oil, oregano oil, parsley (seed) oil, peppermint oil, rosemary oil, sage oil (clary sage, Dalmatian or Spanish sage oil), star aniseed oil, thyme oil, vanilla extract, juniper oil (in particular juniper berry oil), wintergreen oil, cinnamon leaf oil; cinnamon bark oil, and fractions thereof, or constituents isolated therefrom.

It is of particular advantage if the flavoured composition according to the invention comprises at least one flavouring agent, preferably two, three, four, five, six, seven, eight or more flavouring agents chosen from the following group: menthol (preferably I-menthol and/or racemic menthol), anethole, anisole, anisaldehyde, anisyl alcohol, (racemic) neomenthol, eucalyptol (1,8-cineol), menthone (preferably L-menthone), isomenthone (preferably D-isomenthone), isopulegol, menthyl acetate (preferably L-menthyl acetate), menthyl propionate, carvone (preferably (−)-carvone, optionally as a constituent of a spearmint oil), methyl salicylate (optionally as a constituent of a wintergreen oil), eugenol acetate, isoeugenol methyl ether, beta-homocyclocitral, eugenol, isobutyraldehyde, 3-octanol, dimethyl sulfide, hexanol, hexanal, trans-2-hexenal, cis-3-hexenol, 4-terpineol, piperitone, linalool, 8-ocimenyl acetate, isoamyl alcohol, isovaleraldehyde, alpha-pinene, beta-pinene, limonene (preferably D-limonene, optionally as a constituent of an essential oil), piperitone, transsabinene hydrate, menthofuran, caryophyllene, germacrene D, cinnamaldehyde, mint lactone, thymol, gamma-octalactone, gamma-nonalactone, gamma-decalactone, (1,3E,5Z)undecatriene, 2-butanone, ethyl formate, 3-octyl acetate, isoamyl isovalerate, cis- and trans-carvyl acetate, p-cymol, damascenone, damascone, cis-rose oxide, trans-rose oxide, fenchol, acetaldehyde diethyl acetal, 1-ethoxyethyl acetate, cis-4-heptenal, cis-jasmone, methyl dihydrojasmonate, 2'-hydroxypropiophenone, menthyl methyl ether, myrtenyl acetate, 2-phenylethyl alcohol, 2-phenylethyl isobutyrate, 2-phenylethyl isovalerate, geraniol, nerol and viridiflorol.

In particular preferred flavouring compounds encompass menthol, cineol, eugenol, thymol, cinnamic aldehyde, peppermint oil, spearmint oil, eucalyptus oil, thyme oil, cinnamon oil, clove oil, spruce needle oil, fennel oil, sage oil, aniseed oil, star anise oil, chamomile oil, and caraway oil, and their mixtures. In the U.S., fruit flavours, especially cherry, grape, citrus and berry are preferred in the inventive compositions, especially for pediatric products.

The most preferred flavour modulating compounds are selected from the group consisting of vanillin, cis- or trans-pellitorine, hesperetin, matairesinol, and phloretin.

The aroma or flavouring compounds can be present in amounts of about 0.1 to about 5% by weight, preferably about 0.5 to about 3% by weight and in particular about 1 to about 2% by weight.

For flavour solutions, 1,2-propandiol is often used as a solvent. 1,2-propandiol, however, exhibits some intrinsic bitterness. The bitterness of said solvent as well as the bitterness of guaifenesin in the inventive composition can be further reduced by replacing 1,2-propandiol in such a flavour solution by 1,3-propandiol, as it is demonstrated by the following application examples. Therefore, flavour formulations with 1,3-propandiol are preferred over the same formulations with 1,2-propandiol.

A further variant of the first aspect of the invention relates to a composition for oral application.

The composition according to the present invention may be administered orally and may be in the form of a liquid, in solid form or in the form of an aerosol.

A further variant of the invention as described by the first aspect relates to a composition in the form of a liquid, in particular a syrup, in solid form, in particular a powder, or a tablet, in particular a chewable tablet, an effervescent tablet, a capsule, a gel, a gum or in the form of an aerosol.

In the case of liquid formulations, water, water-ethanol-mixture or ethanol as liquid/solvent is preferred. The liquid formulations are preferably selected from the group consisting of a syrup, a solution and a suspension. If the composition according to the present invention is administered in a solid form, the solid could be for example a powder, a capsule, a pill, a pastille or a hard-boiled candy form. The composition may also take the form of a gel or a gum.

The invention also may be used in aerosol formulations which are to be inhaled into the lungs. Among such formulations with water, water-ethanol-mixtures or ethanol as liquid medium or propellant driven are preferred.

As an alternative to powders, tablets may be used. In the case of a tablet, in particular, a chewable tablet or an effervescent tablet is preferred. The ingredients may be the same. In a preferred embodiment of the present invention, the powder formulation or composition is used as it is or can also be pressed to a tablet and—as needed—be dissolved in water, for example as an effervescent powder or tablet. In such an embodiment, the tablet—just as the powder formulation—may additionally comprise an effervescent agent such as bicarbonate.

In order to ensure that the patient can easily prepare a drinkable liquid formulation, the inventive composition or formulation can be delivered in separate packages. In these packages, water and the inventive composition or formulation are stored separately from each other. The package further allows both components to be mixed in an easy way.

As a consequence thereof, the present invention also relates to a kit of parts comprising two components, (a) the composition or formulation according to the invention and (b) water or alternatively a drinkable fluid like a juice, both components separated from each other.

To solve this issue, for example bottles having special caps can be used. Most often in such packages, the liquid solvent can be stored in a bottle of glass, plastic, metal and so on while the cap for closing the bottle comprises a chamber to take the composition or formulation of the present invention. Prior to use, the patient can take out the powder of the cap and mix it with the water in the bottle. This mixing process can either be done consciously, meaning the patient actively takes the powder and puts it into the water. In other embodiments, the patient can initiate the mixing process in a more automatic way by for example just screwing, pressing, shaking the cap or the bottle, in order to remove a barrier in the chamber containing the powder and by doing so allowing it to fall from the cap into the bottle. Other, similar devices might be used, too. Besides, the inventive composition or formulation can be stored in an aluminium or plastic-bag or in an aluminium or plastic bottle. The thus stored powder then can be used with a pre-metered amount of water, stored in another package or with freshly filled drinking water, tap water or carbonized water.

In a second aspect of the present invention, the afore described composition is used as a medicament or applied in medical use. Additionally, the composition may be used for the preparation of a medicament.

Another variant of the second aspect relates to the use of the medical composition, preferably in the prevention or treatment of respiratory diseases, in particular the common cold, cough or catarrh which come along with bronchial secretions and mucolytics, in particular for the use as an expectorant. The medical composition helps to loosen viscous bronchial secretions and to reduce the thickness or viscosity of bronchial secretions, thus increasing mucus flow that can be removed more easily through coughing.

Disclosed is also the use of the composition according to the present invention for the treatment of respiratory diseases, in particular, the common cold, cough or catarrh which come along with bronchial secretions and mucolytics. Preferably the composition according to the present invention is used as an expectorant.

Additionally, in another aspect of the present invention, the composition according to the present invention is used for the preparation of a pharmaceutical composition. These pharmaceutical compositions comprise both compositions which are non-prescription drugs and sold over the counter and compositions which are only available on prescription.

Finally, in a third aspect of the present invention, the use of one or more flavour compound(s) containing an isovanillyl group for masking or inhibiting the bitter taste of guaifenesin or compositions comprising guaifenesin is described.

Surprisingly, it was found that the bitter taste of guaifenesin may be masked or even inhibited by at least one flavour compound containing an isovanillyl group used according to the present invention.

EXPERIMENTAL SECTION

Example 1: Effect of Hesperetin and Phyllodulcin on Guaifenesin-Induced Acid Secretion in HGT-1 Cells Human gastric tumour cell line 1 (HGT-1; Laboisse C. L.; Augeron C.; Couturier-Turpin M. H.; Gespach C.; Cheret A. M.; Potet F., Characterization of a newly established human gastric cancer cell line HGT-1 bearing histamine H2-receptors, Canc. Res., 1982, 42, 1541 to 1548) is a suitable screening tool for detecting the interaction of bitter agents and bitter modulating substances (Liszt, K. I.; Hans, J.; Ley, J. P.; Kock, E.; Somoza, V., Characterization of bitter compounds via modulation of proton secretion in human gastric parietal cells in culture, J. Agric. Food Chem., 2018, 66 (10), 2295-2300.). Therefore, the effect of hesperetin and phyllodulcin on guaifenesin-induced acid secretion in the HGT-1 cell line was determined to predict the modulation of guaifenesin-induced bitterness by hesperetin and phyllodulcin. To this aim, HGT-1 cells were cultured under standard conditions and passaged at ca. 80% confluence. Cells were then seeded into 96-well plates at a density of $10^5/cm^2$ and used for measurements when 80% confluence was reached in the wells. HGT-1 cells were pre-loaded with (acetyloxy)methyl-3-(acetyloxy)-10-(dimethylamino)-3'-oxo-spiro[7H-benzo[c]xanthene-7,1'(3H)-isobenzofuran]-ar'-carboxylate and incubated in 130 mM NaCl 130, 4.7 mM KCl, 1.3 mM $CaCl_2$), 1.2 mM $MgSO_4$, 1.2 mM $KH_2PO_4$, 11.7 mM glucose, 10 mM HEPES 10, 20 µM 4,4'-Diisothiocyanatostilbene-2,2'-disulfonic acid disodium and 20 µM 5-(N-Ethyl-N-isopropyl)amiloride at pH 7.4. Fluorescence recordings were performed with an excitation wavelength of 488 nm and monitoring the emission wavelengths of 580 nm and 640 nm, respectively, each with a 20 nm bandwidth. Recordings were performed over 5 min and raw data was converted into the log 2 transformed ratio of treated versus untreated cells.

Co-incubation of 10 mM guaifenesin with 30 µM hesperetin or alternatively 30 µM phyllodulcin resulted in a significant decrease in proton secretory activity of HGT-1 cells from 10 min onwards compared to cells incubated with 10 mM guaifenesin alone (Table 1 and FIGS. 1 and 2).

TABLE 1

| Time-point [min] | Control | SEM Control | 10 mM guaifenesin | SEM 10 mM guaifenesin | 10 mM guaifenesin + 30 μM phyllodulcin | SEM 10 mM guaifenesin + 30 μM phyllodulcin |
|---|---|---|---|---|---|---|
| 0 | 0.003149971 | 0.026862612 | 0.271079754 | 0.044113387 | −0.081652667* | 0.030632578 |
| 5 | 0.007061932 | 0.027042744 | 0.237794014 | 0.033451679 | 0.057895647*** | 0.042773859 |
| 10 | 0.015620808 | 0.022133786 | 0.280094783 | 0.044475484 | 0.072935281*** | 0.047787243 |
| 15 | 0.029742689 | 0.029510524 | 0.217782136 | 0.036244094 | −0.041719718 | 0.070934298 |
| 20 | 0.051826461 | 0.022214979 | 0.322955114 | 0.032614147 | 0.085121528* | 0.035691727 |
| 25 | 0.039027114 | 0.03549437 | 0.395261045 | 0.04385823 | −0.146876109 | 0.075694763 |
| 30 | 0.014020312 | 0.025787733 | 0.270624267 | 0.03847183 | 0.143271078*** | 0.051611841 |

TABLE 2

| Time-point [min] | Control | SEM Control | 10 mM guaifenesin | SEM 10 mM guaifenesin | 10 mM guaifenesin + 30 μM hesperetin | SEM 10 mM guaifenesin + 30 μM hesperetin |
|---|---|---|---|---|---|---|
| 0 | 0.046874281 | 0.022932377 | 0.259638649 | 0.03348251 | −0.132041167 | 0.038336276 |
| 5 | 0.013089094 | 0.019714875 | 0.247524958 | 0.024484355 | 0.057353437*** | 0.034118058 |
| 10 | 0.002916978 | 0.019537202 | 0.186969061 | 0.036444678 | −0.043285573* | 0.032175504 |
| 15 | −0.00892491 | 0.022154965 | 0.225860563 | 0.03028256 | 0.039545736*** | 0.031214134 |
| 20 | 0.012958172 | 0.017223774 | 0.264993538 | 0.027857927 | 0.002333741*** | 0.035033075 |
| 25 | 0.024853898 | 0.019495572 | 0.186077754 | 0.039967907 | 0.015765819*** | 0.031509482 |
| 30 | 0.020479352 | 0.023231257 | 0.247336833 | 0.042970717 | 0.025917217*** | 0.034931911 |

The data in Table 1 and Table 2 are presented as mean±SEM derived from 3 biological replicates and 6 to 9 technical replicates. Outliers were identified using the Nalimov test, statistical significance was tested one-way ANOVA with Tukey's range test for multiple comparisons and Bonferroni correction, establishing the threshold for significance at $p<0.01$. Accordingly, data are marked with *($p<0.007$), ($p<0.001$) or *($p<0.0001$). Control: untreated cells Example 2: Sensory Effect of Hesperetin and Phyllodulcin on Guaifenesin-Induced Bitterness Perception To verify the effect of hesperetin and phyllodulcin on guaifenesin-induced bitterness perception, an aqueous solution of 1.3 g/l guaifenesin (1) was tested against an aqueous solution containing 1.3 g/l guaifenesin and 100 mg/l hesperetin (2) or 7 mg/l phyllodulcin (3) or 100 mg/l homoeriodictyol as comparison (4). The test was conducted as a randomized comparison test in a trained sensory panel (n=20 to 30) via a sip and spit procedure. The panellists tasted both solutions in a blinded fashion and rated bitterness on a scale of 0 to 100. The relative differences in the bitter ratings are shown in table 3.

TABLE 3

| | Example | Modulation versus control |
|---|---|---|
| 1 (Control) | 1.3 g/l guaifenesin | −/− |
| 2 | 1.3 g/l guaifenesin + 100 mg/l hesperetin (racemic) | −25% |
| 3 | 1.3 g/l guaifenesin + 7 mg/l (3R)-phyllodulcin (98 weight %, 95 mol % enantiomeric purity) | −15% |

TABLE 3-continued

| | Example | Modulation versus control |
|---|---|---|
| 4 (for comparison with state of the art technology) | 1.3 g/l guaifenesin + 100 mg/l homoeriodictyol (racemic) | −12% |

APPLICATION EXAMPLES

Application Example 1: Syrup

Preparation of a syrup containing 100 mg guaifenesin/dose according to the following recipe:

| Constituent | Content in % (w/w) | | |
|---|---|---|---|
| | A | B | C |
| Guaifenesin | 1.25 | 1.25 | 1.25 |
| 1,2-propandiol | 23 | 23 | 23 |
| Glycerol | 8 | 8 | 8 |
| Sorbitol | 13.15 | 13.15 | 13.15 |
| Xanthan Gum | 0.2 | 0.2 | 0.2 |
| Symrise Aroma Type Strawberry | 0.4 | — | — |
| Symrise Aroma Type Strawberry containing 0.36% hesperetin with 1,2-propandiol as solvent | — | 0.4 | — |
| Symrise Aroma Type Strawberry containing 0.10% phyllodulcin with 1,2-propandiol as solvent | — | — | 0.4 |
| Water | add to 100 | add to 100 | add to 100 |

All syrups were thoroughly mixed until all constituents were dissolved completely. Syrup B and syrup C were significantly less bitter than syrup A.

Application Example 2: Powder Formulation

Preparation of a powder formulation containing 75 mg guaifenesin/dose according to the following recipe:

| Constituent | Content in % (w/w) | | |
| --- | --- | --- | --- |
| | A | B | C |
| Guaifenesin | 1.5 | 1.5 | 1.5 |
| Citric acid | 3 | 3 | 3 |
| Saccharin sodium | 2.5 | 2.5 | 2.5 |
| Ascorbic acid | 1 | 1 | 1 |
| Symrise Aroma Type Lemon | 0.8 | — | — |
| Symrise Aroma Type Lemon containing 0.18% hesperetin | — | 0.8 | — |
| Symrise Aroma Type Lemon containing 0.05% phyllodulcin | — | — | 0.8 |
| Sucrose | add to 100 | add to 100 | add to 100 |

All powders were dry mixed and sieved. Powder B and powder C were significantly less bitter than powder A.

Application Example 3: Chewable Tablets

Preparation of chewable tables (2 g) with 100 mg guaifenesin/dose according to the following recipe:

| Constituent | Content in % (w/w) | |
| --- | --- | --- |
| | A | B |
| Guaifenesin | 1 | 1 |
| Calcium carbonate | 25 | 25 |
| Magnesium stearate | 0.5 | 0.5 |
| Citric acid | 0.75 | 0.75 |
| Symrise Aroma Type Orange | 0.8 | — |
| Symrise Aroma Type Orange containing 0.18% hesperetin | — | 0.8 |
| Sucralose | 0.075 | 0.075 |
| Dextrose | add to 100 | add to 100 |

All constituents were thoroughly mixed and left to rest for 1 to 2 hrs, then tablets were pressed. Formulation B was less bitter than formulation A.

Application Example 4: Effervescent Tablets

Preparation of effervescent tablets with 50 mg guaifenesin per dose according to the following recipe:

| Constituent | Content in % (w/w) | | |
| --- | --- | --- | --- |
| | A | B | C |
| Guaifenesin | 1 | 1 | 1 |
| Sorbitol | 8.4 | 8.4 | 8.4 |
| Sodium cyclamate | 1.5 | 1.5 | 1.5 |
| Sucralose | 0.25 | 0.25 | 0.25 |
| Symrise Aroma Type Lemon | 0.4 | — | — |
| Symrise Aroma Type Lemon containing 0.36% hesperetin | — | 0.4 | — |
| Symrise Aroma Type Lemon containing 0.05% phyllodulcin | — | — | 0.4 |
| 1,3-propandiol | 0.625 | 0.625 | 0.625 |

All constituents are thoroughly mixed and then filled to 100% with a premix of sodium hydrogencarbonate and citric acid (in a ratio of 1:1 0.36 (w/w)). The mixture is left to rest for 1 to 2 hrs and then sieved and subsequently pressed into tablets. Formulation B and formulation C exhibited reduced bitterness compared to formulation A.

Application Example 5: Fruit Gums

Preparation of fruit gums containing 75 mg guaifenesin/dose according to the following recipe:

| Constituent | Content in % (w/w) | | |
| --- | --- | --- | --- |
| | A | B | C |
| Guaifenesin | 1.5 | 1.5 | 1.5 |
| Gelatine 240 Bloom | 7.6 | 7.6 | 7.6 |
| Saccharose | 34.50 | 34.50 | 34.50 |
| Glucose syrup, DE 40 | 31.89 | 31.89 | 31.89 |
| Iso Syrup C* Tru Sweet 01750 (Cerestar GmbH) | 1.50 | 1.50 | 1.50 |
| Yellow and red coloring | 0.01 | | |
| Citric acid | 0.2 | | |
| Symrise Aroma Type Raspberry | 0.4 | — | — |
| Symrise Aroma Type Raspberry containing 0.36% hesperetin with 1,2-propandiol as solvent | — | 0.4 | — |
| Symrise Aroma Type Raspberry containing 0.05% phyllodulcin with 1,2-propandiol as solvent | — | — | 0.4 |
| Water | add to 100 | add to 100 | add to 100 |

Formulation B and formulation C exhibited considerably reduced bitterness compared to formulation A.

Application Example 6: Throat Candies with a Liquid-Viscous Core Filling (Centre-Filled Hard Candy)

| Constituent | Content in % (w/w) | |
| --- | --- | --- |
| | A | B |
| Part A (shell) (80% of the candy) | | |
| Sugar (sucrose) | add to 100 | add to 100 |
| Glucose syrup (solids content 80%) | 41.51 | 49.37 |
| Mixture X1 of EP 2 187 871 B1 | 0.75 | 0.95 |
| l-Menthol | 0.10 | — |
| Lemon oil | 0.10 | 0.10 |
| Citric acid | — | 0.91 |
| Total A: | 100 | 100 |

-continued

| Constituent | Content in % (w/w) | |
|---|---|---|
| | A | B |
| Part B (core) (20% of the candy) | | |
| High fructose corn syrup (content of solid sugars 85%, close to 15% water) | add to 100 | add to 100 |
| Glycerol | 15.0 | 15.0 |
| Lecithin | 0.02 | 0.02 |
| Guaifenesin | 5 | 5 |
| Pellitorin | 0.10 | 0.25 |
| Capsaicin | 0.05 | — |
| Homovanillic acid ethylester analogous to EP 2 932 858 | — | 0.50 |
| Red dyestuff, as a 5% strength aqueous solution | 0.20 | 0.20 |
| hesperetin, 5% in 1,2-propandiol; and phyllodulcin, 1.25% in 1,2-propandiol | 0.1 | 0.1 |
| Total B: | 100 | 100 |

Bonbons having a liquid-viscous core were prepared in accordance with the processes described in U.S. Pat. No. 6,432,441 (Example 1) and in U.S. Pat. Nos. 5,458,894 and 5,002,791. The two parts A and B were processed separately to bases for the shell (Part A) and the core (Part B). The filled throat candies obtained by means of co-extrusion acted against coughing, sore throat and hoarseness when consumed by affected persons.

The invention claimed is:

1. Composition comprising:
 (a) guaifenesin or one or more of its derivatives or isomers or mixtures thereof, and
 (b) one or more flavour compound(s) containing an isovanillyl group or one or more of its derivatives or isomers or mixtures thereof;
 and optionally
 (c) at least one pharmaceutically acceptable adjuvant or additive
 wherein the derivatives of guaifenesin or the one or more flavour compound(s) containing an isovanillyl group are selected from the group consisting of the salts, esters and mixtures thereof; and
 wherein the one or more flavour compound(s) containing an isovanillyl group is/are selected from the group of hesperetin, hesperetindihydrochalcone, hesperetindihydrochalcone-4'-O-glucoside and phyllodulcin; and
 wherein the composition comprises guaifenesin in an amount of from 2000 to 20000 ppm.

2. The composition according to claim 1, comprising the one or more flavour compound(s) containing an isovanillyl group in a total amount of 4 to 400 ppm.

3. The composition according to claim 1, comprising component (a) and component (b) in a ratio (w/w) in a range of 5:1 to 5000:1.

4. The composition according to claim 1, further comprising homoeriodictyol or its derivatives or isomers or mixtures thereof, wherein a derivative is selected from the group consisting of the salts, esters and mixtures thereof.

5. The composition according to claim 1, further comprising one or more pharmaceutically effective compounds.

6. The composition according to claim 1, wherein the at least one adjuvant is selected from one or more in the group of carriers, solvents, emulsifiers, dispersing agents, synthetic and natural biopolymers, stabilizers, colourings, pH-adjusting agents, flow agents, disintegrants, odour-correcting agents and taste-correcting agents.

7. The composition according to claim 1, in a form suitable for oral application.

8. The composition according to claim 1 in the form of a liquid, a solid, a gel, a gum or an aerosol.

9. A method of using the composition according to claim 1, comprising administering the composition of claim 1 to a subject in need thereof.

10. A method of using the composition according to claim 1, comprising administering the composition of claim 1 to a subject for the prevention or treatment of a respiratory disease.

11. A method of using one or more flavour compounds containing an isovanillyl group for masking or inhibiting the bitter taste of guaifenesin or of guaifenesin-comprising compositions, wherein the one or more flavour compound(s) containing an isovanillyl group is/are selected from the group of hesperetin, hesperetindihydrochalcone, hesperetin-dihydrochalcone-4'-O-glucoside and phyllodulcin, wherein guaifenesin is present in an amount o from 2000 to 20000 ppm.

12. The method of claim 11, comprising compounding the one or more flavour compounds containing an isovanillyl group with guaifenesin or a guaifenesin-containing composition.

13. The composition according to claim 5, wherein the one or more pharmaceutically effective compounds is chosen from analgesic agents, anti-inflammatory agents, antitussives, decongestants and antihistamines.

14. The composition according to claim 8, in the form of a syrup.

15. The composition according to claim 8, in the form of a powder, a tablet, or a capsule.

16. The method of claim 10, wherein the subject has a common cold, cough, or catarrh.

17. The method of claim 10, wherein the subject is in need of an expectorant.

\* \* \* \* \*